United States Patent [19]

Fauran et al.

[11] 4,061,855
[45] Dec. 6, 1977

[54] PYRIMIDIN-6-YL ACETHYDROXAMIC ACIDS

[75] Inventors: Claude P. Fauran, Paris; Jeannine A. Eberle, Chatou; Guy R. Bourgery, Colombes; Guy R. Raynaud, Paris; Claude J. Gouret, Meudon, all of France

[73] Assignee: Delalande S.A., Courbevoie, France

[21] Appl. No.: 749,221

[22] Filed: Dec. 10, 1976

Related U.S. Application Data

[62] Division of Ser. No. 554,532, March 3, 1975, Pat. No. 4,013,768.

[30] Foreign Application Priority Data

Mar. 19, 1974 France .................................. 74.09235

[51] Int. Cl.² .................. C07D 413/12; A61K 31/535
[52] U.S. Cl. ........................... 544/122; 424/248.54
[58] Field of Search ........................ 260/247.2 A; 424/248.54

[56] References Cited

U.S. PATENT DOCUMENTS 4,013,768   3/1977   Fauran et al. ..................... 424/251

Primary Examiner—Henry R. Jiles
Assistant Examiner—R. Ramsuer
Attorney, Agent, or Firm—Blanchard, Flynn, Thiel, Boutell & Tanis

[57] ABSTRACT

Compounds of the formula

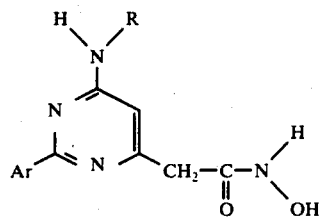

in which R is aminocarbonylphenyl in which amino is —NH₂, pyrrolidino, piperidino or morpholino, and Ar is phenyl substituted with chloro, fluoro, trifluoromethyl, methylenedioxy or one or more methoxy. The compounds are prepared by reacting 2-Ar-4-chloropyrimidin-6-yl ethylacetate with

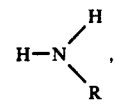

and then reacting that reaction product with hydroxylamine hydrochloride. The compounds possess vasodilatatory, anti-ulcerous, respiratory analeptic, hypotensive, diuretic, anti-depressive, analgesic, anti-inflammatory and neurotropic properties.

6 Claims, No Drawings

PYRIMIDIN-6-YL ACETHYDROXAMIC ACIDS

CROSS REFERENCE TO RELATED APPLICATION

This is a division, of application Ser. No. 554,532, filed Mar. 3, 1975 now U.S. Pat. No. 4,013,768.

This application relates to our U.S. patent application Ser. No. 299,672, filed Oct. 24, 1972, now U.S. Pat. No. 3,876,636, issued Apr. 8, 1975.

Our U.S. Ser. No. 299,672, filed Oct. 24, 1972, now U.S. Pat. No. 3,876,636, issued Apr. 8, 1975 discloses pyrimidin-6-yl acethydroxamic acids, corresponding to the general formula Io.

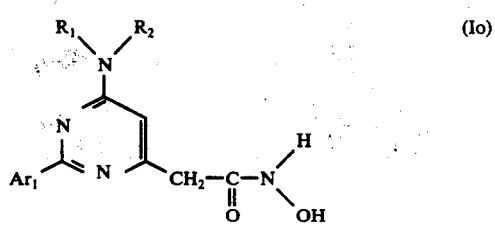

in which:

$R_1$ and $R_2$ are each alkyl radicals having 1 to 3 carbon atoms or form, together with the nitrogen atom to which they are attached, a heterocyclic radical selected from the radicals: pyrrolidino, piperidino, hexamethyleneimino and morpholino, and $Ar_1$ represents a phenyl radical which may be mono or polysubstituted, by a halogen atom selected from fluorine, chlorine and bromine, by a methoxy or a methylcarbonyloxy radical, by a $CF_3$ residue or by a methylenedioxy radical.

The present addition concerns compounds of the same type, corresponding to the formula I:

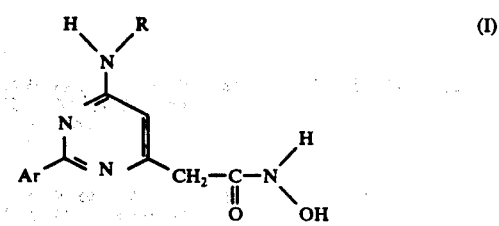

in which:

R represents an aminocarbonylphenyl radical, in which the amino group may be primary or tertiary and carrying, in the latter case, a heterocyclic radical selected from the following: pyrrolidino, piperidino and morpholino; and Ar represents a phenyl ring substituted by a halogen atom selected from chlorine and fluorine, by a trifluoromethyl group, by a methylenedioxy radical or by one or more methoxy groups.

The process according to the invention consists in reacting an acetic ester of formula II:

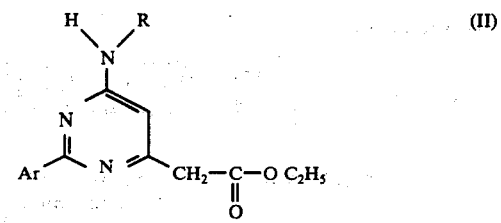

with hydroxylamine hydrochloride of formula III:

$NH_2OH, HCl$         (III)

R and Ar having in formula II, the same significance as in formula I.

The reaction is effected in a methanolic medium, at the reflux temperature of methanol, and in the presence of sodium methylate.

The acetic esters of formula II are obtained by condensation of a derivative of (4-chloro-pyrimidin-6-yl) ethyl acetate of formula IV:

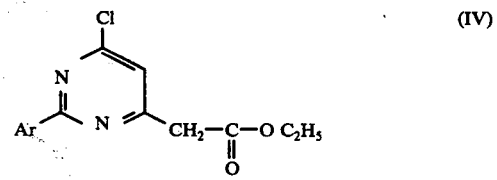

with an amine of formula V:

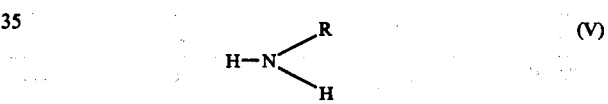

R and Ar having in these formulas the same significance as in formula (I).

The condensation is conducted in an acetic acid medium at 80° – 90° C and in the presence of concentrated hydrochloric acid.

The following preparation is given by way of example to illustrate the invention.

EXAMPLE:

[(2-p-chlorophenyl 4-p-aminocarbonylanilino) pyrimidin-6-yl] acethydroxamic acid.

Code No. 72 553

1st Stage: [(2-p-chlorophenyl-4-p-aminocarbonyl anilino) pyrimidin-6-yl] ethyl acetate.

Code No. 72 333

A solution of 93.5g (0.3 mol) of (2-p-chlorophenyl-4-chloro) pyrimidin-6-yl ethyl acetate, 40.8g (0.3 mol) of p-aminocarbonyl aniline and 1.5 c.c. of concentrated hydrochloric acid in 600 c.c. of acetic acid, is heated for one hour at 90° C. The solution is then diluted with 2 l of water and alkalinised with concentrated ammonia. The product is filtered and recrystallized from 2 l of methanol.

83 g. of product are recovered, which corresponds to a yield of 68%.

Empirical formula: $C_{21}H_{19}Cl\ N_4O_3$

Elementary analysis:

| | C | H | N |
|---|---|---|---|
| Calculated % | 61.39 | 4.66 | 13.64 |
| Found % | 61.37 | 4.76 | 13.47 |

2nd Stage: [(2-p-chlorophenyl-4-p-aminocarbonyl anilino) pyrimidin-6-yl] acethydroxamic acid.
Code No. 72 553

A solution of 10.4g (0.15 mol) of hydroxylamine hydrochloride in 150 c.c. of methanol is added to a solution of 6.9g. of sodium in 200 c.c. of methanol. The mixture is left for 30 minutes, and then the salt formed is filtered off. 61.5g. (0.15 mol) of the ester obtained in the preceding stage is added to the filtrate and the suspension formed is heated under reflux for 2½ hours. The mixture is then diluted with 1 l of water and acidified just to a pH of about 3 with concentrated hydrochloric acid and returned to neutrality by adding a solution of sodium bicarbonate. The product is filtered and recrystallized from 400 c.c. of 90% alcohol.

11 g of product is obtained, which corresponds to a yield of 20%.

Empirical formula: $C_{19}H_{16}Cl\ N_5O_3$

Elementary analysis:

| | C | H | N |
|---|---|---|---|
| Calculated % | 57.36 | 4.05 | 17.61 |
| Found % | 57.19 | 4.14 | 17.44 |

The compounds listed in the following Tables I and II have been prepared according to the mode of operation of the first and second stages of the Example, respectively.

TABLE I

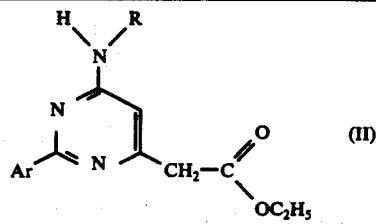

(II)

| Code No. | Ar | R | Empirical Formula | Molecular Weight | Melting Point (°C) | Yield (%) | Elementary Analysis | | | |
|---|---|---|---|---|---|---|---|---|---|---|
| | | | | | | | | C | H | N |
| 72 242 | Cl-C₆H₄- | -C(O)-C₆H₄-NH₂ | $C_{21}H_{19}ClN_4O_3$ | 410.85 | 218 | 83 | Calc. % | 61.39 | 4.66 | 13.64 |
| | | | | | | | Found % | 61.31 | 4.54 | 13.83 |
| 72 223 | Cl-C₆H₄- | pyrrolidinyl-C(O)-C₆H₄- | $C_{25}H_{25}ClN_4O_3$ | 464.94 | 209 | 64 | Calc. % | 64.58 | 5.42 | 12.05 |
| | | | | | | | Found % | 64.59 | 5.55 | 11.91 |
| 72 244 | Cl-C₆H₄- | morpholinyl-C(O)-C₆H₄- | $C_{25}H_{25}ClN_4O_4$ | 480.94 | 204 | 58 | Calc. % | 62.43 | 5.24 | 11.65 |
| | | | | | | | Found % | 62.40 | 5.33 | 11.43 |
| 72 232 | Cl-C₆H₄- | piperidinyl-C(O)-C₆H₄- | $C_{25}H_{27}ClN_4O_3$ | 478.96 | 185 | 61 | Calc. % | 65.19 | 5.68 | 11.70 |
| | | | | | | | Found % | 65.23 | 5.90 | 11.77 |
| 72 369 | 3-Cl-C₆H₄- | -C(O)-C₆H₄-NH₂ | $C_{21}H_{19}ClN_4O_3$ | 410.85 | 179 | 53 | Calc. % | 61.39 | 4.66 | 13.64 |
| | | | | | | | Found % | 61.59 | 4.74 | 13.56 |
| 72 699 | F-C₆H₄- | -C(O)-C₆H₄-NH₂ | $C_{21}H_{19}FN_4O_3$ | 394.39 | 166 | 56 | Calc. % | 63.95 | 4.86 | 14.21 |
| | | | | | | | Found % | 64.06 | 4.67 | 14.30 |

TABLE I-continued

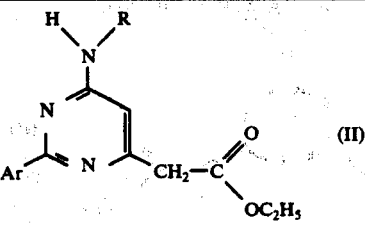

(II)

| Code No. | Ar | R | Empirical Formula | Molecular Weight | Melting Point (°C) | Yield (%) | Elementary Analysis | C | H | N |
|---|---|---|---|---|---|---|---|---|---|---|
| 72 735 | $F_3C$-phenyl | benzamide (ortho) | $C_{22}H_{19}F_3N_4O_3$ | 444.40 | 180 | 63 | Calc. % / Found % | 59.45 / 59.42 | 4.31 / 4.35 | 12.61 / 12.42 |
| 72 746 | $F_3C$-phenyl | benzamide (para) | $C_{22}H_{19}F_3N_4O_3$ | 444.40 | 191 | 56 | Calc. % / Found % | 59.45 / 59.25 | 4.31 / 4.44 | 12.61 / 12.55 |
| 72 728 | $F_3C$-phenyl | pyrrolidinyl-carbonyl-phenyl | $C_{26}H_{25}F_3N_4O_3$ | 498.49 | 204 | 63 | Calc. % / Found % | 62.64 / 62.70 | 5.06 / 5.25 | 11.24 / 11.08 |
| 72 193 | $F_3C$-phenyl | morpholinyl-carbonyl-phenyl | $C_{26}H_{25}F_3N_4O_4$ | 514.49 | 188 | 44 | Calc. % / Found % | 60.69 / 60.63 | 4.90 / 4.95 | 10.89 / 10.93 |
| 72 729 | $F_3C$-phenyl | piperidinyl-carbonyl-phenyl | $C_{27}H_{27}F_3N_4O_3$ | 512.52 | 181 | 58 | Calc. % / Found % | 63.27 / 63.23 | 5.31 / 5.35 | 10.93 / 11.07 |
| 72 567 | 2,4,5-tri-$H_3CO$-phenyl | benzamide (ortho) | $C_{24}H_{26}N_4O_6$ | 466.48 | 164 | 66 | Calc. % / Found % | 61.79 / 61.71 | 5.62 / 5.75 | 12.01 / 11.83 |
| 72 566 | 2,4,5-tri-$H_3CO$-phenyl | benzamide (para) | $C_{24}H_{25}N_4O_6$ | 466.48 | 238 | 38 | Calc. % / Found % | 61.79 / 61.72 | 5.62 / 5.76 | 12.01 / 11.97 |
| 72 587 | 2,4,5-tri-$H_3CO$-phenyl | morpholinyl-carbonyl-phenyl | $C_{28}H_{32}N_4O_7$ | 536.57 | 200 | 80 | Calc. % / Found % | 62.67 / 62.70 | 6.01 / 6.04 | 10.44 / 10.39 |
| 72 586 | 2,4,5-tri-$H_3CO$-phenyl | piperidinyl-carbonyl-phenyl | $C_{29}H_{34}N_4O_6$ | 534.57 | 160 | 65 | Calc. % / Found % | 65.16 / 65.06 | 6.41 / 6.44 | 10.48 / 10.45 |

TABLE I-continued

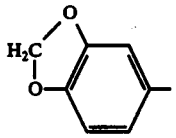

| Code No. | Ar | R | Empirical Formula | Molecular Weight | Melting Point (°C) | Yield (%) | Elementary Analysis | | | |
|---|---|---|---|---|---|---|---|---|---|---|
| | | | | | | | | C | H | N |
| 730030 | 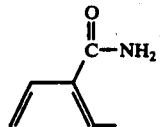 | 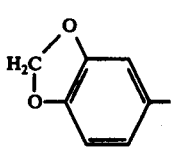 | $C_{22}H_{20}N_4O_5$ | 420.41 | 178 | 80 | Calc. % | 62.85 | 4.80 | 13.33 |
| | | | | | | | Found % | 62.66 | 4.98 | 13.13 |
| 730055 | 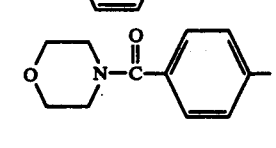 |  | $C_{26}H_{26}N_4O_6$ | 490.49 | 179 | 17 | Calc. % | 63.66 | 5.34 | 11.42 |
| | | | | | | | Found % | 63.55 | 5.42 | 11.22 |

TABLE II

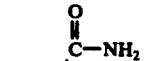

| Code No. | Ar | R | form | Empirical formula | Molecular weight | Melting point (°C) | Yield (%) | Elementary analysis | | | |
|---|---|---|---|---|---|---|---|---|---|---|---|
| | | | | | | | | | C | H | N |
| 72 583 | 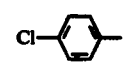 | 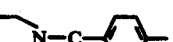 | base | $C_{19}H_{16}ClN_5O_3$ | 397.81 | 260 | 37 | Calc. % | 57.36 | 4.05 | 17.61 |
| | | | | | | | | Found % | 57.45 | 4.25 | 17.41 |
| 72 319 |  | | base | $C_{23}H_{22}ClN_5O_3$ | 451.90 | 203 | 20 | Calc. % | 61.13 | 4.91 | 15.50 |
| | | | | | | | | Found % | 60.98 | 5.20 | 15.33 |
| 72 308 | | | base | $C_{24}H_{24}Cl N_5O_3$ | 465.93 | 220 | 30 | Calc. % | 61.86 | 5.12 | 15.03 |
| | | | | | | | | Found % | 61.86 | 5.24 | 14.87 |
| 72 506 | 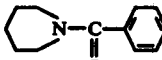 |  | base | $C_{19}H_{16}Cl N_5O_3$ | 397.81 | 230 | 42 | Calc. % | 57.36 | 4.05 | 17.61 |
| | | | | | | | | Found % | 57.52 | 4.18 | 17.45 |
| 72 595 | 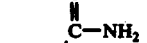 | 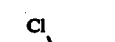 | hydrochloride | $C_{23}H_{23}Cl_2N_5O_3$ | 488.37 | 210 | 29 | Calc. % | 56.56 | 4.75 | 14.34 |
| | | | | | | | | Found % | 56.77 | 4.72 | 14.15 |
| 72 262 |  |  | base | $C_{23}H_{22}Cl N_5O_4$ | 467.90 | 210 | 30 | Calc. % | 59.04 | 4.74 | 14.97 |
| | | | | | | | | Found % | 58.84 | 4.84 | 14.83 |
| 72 722 |  | 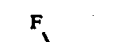 | base | $C_{19}H_{16}F N_5O_3$ | 381.36 | 237 | 52 | Calc. % | 59.84 | 4.23 | 18.37 |
| | | | | | | | | Found % | 59.71 | 4.30 | 18.31 |

TABLE II-continued

Structure (I): Ar-pyrimidine with NHR substituent and CH₂-C(=O)-NH-OH side chain

| Code No. | Ar | R | form | Empirical formula | Molecular weight | Melting point (°C) | Yield (%) | Elementary analysis | C | H | N |
|---|---|---|---|---|---|---|---|---|---|---|---|
| 72 837 | 3-CF₃-C₆H₄ | 2-(H₂N-CO)-C₆H₄- | base | $C_{20}H_{16}F_3N_5O_3$ | 431.37 | 224 | 71 | Calc. % / Found % | 55.68 / 55.56 | 3.74 / 3.91 | 16.24 / 16.09 |
| 72 836 | 3-CF₃-C₆H₄ | 4-(H₂N-CO)-C₆H₄- | base | $C_{20}H_{16}F_3N_5O_3$ | 431.37 | 210 | 64 | Calc. % / Found % | 55.63 / 55.86 | 3.74 / 3.92 | 16.24 / 16.08 |
| 72 753 | 3-CF₃-C₆H₄ | 4-(pyrrolidinyl-CO)-C₆H₄- | base | $C_{24}H_{22}F_3N_5O_3$ | 485.46 | 145 | 49 | Calc. % / Found % | 59.38 / 59.20 | 4.57 / 4.66 | 14.43 / 14.33 |
| 730022 | 3-CF₃-C₆H₄ | 4-(piperidinyl-CO)-C₆H₄- | base | $C_{25}H_{24}F_3N_5O_3$ | 499.48 | 150 | 6 | Calc. % / Found % | 60.11 / 60.41 | 4.84 / 5.27 | 14.02 / 14.14 |
| 72 795 | 3-CF₃-C₆H₄ | 4-(morpholinyl-CO)-C₆H₄- | base | $C_{24}H_{22}F_3N_5O_4$ | 501.46 | 160 | 7 | Calc. % / Found % | 57.48 / 57.57 | 4.42 / 4.54 | 13.97 / 13.82 |
| 72 601 | 3,4,5-tri-OCH₃-C₆H₂ | 2-(H₂N-CO)-C₆H₄- | base | $C_{22}H_{23}N_5O_6$ | 453.44 | 222 | 31 | Calc. % / Found % | 58.27 / 58.48 | 5.11 / 5.11 | 15.45 / 15.27 |
| 72 791 | 3,4,5-tri-OCH₃-C₆H₂ | 4-(H₂N-CO)-C₆H₄- | base | $C_{22}H_{23}N_5O_6$ | 453.44 | 210 | 17 | Calc. % / Found % | 58.27 / 58.07 | 5.11 / 5.31 | 15.43 / 15.34 |
| 72 635 | 3,4,5-tri-OCH₃-C₆H₂ | 4-(morpholinyl-CO)-C₆H₄- | base | $C_{26}H_{29}N_5O_7$ | 523.53 | 198 | 44 | Calc. % / Found % | 59.64 / 59.44 | 5.58 / 5.51 | 13.38 / 13.20 |
| 72 629 | 3,4,5-tri-OCH₃-C₆H₂ | 4-(piperidinyl-CO)-C₆H₄- | base | $C_{27}H_{31}N_5O_6$ | 521.56 | 179 | 28 | Calc. % / Found % | 62.17 / 62.37 | 5.99 / 5.87 | 13.43 / 13.30 |
| 730056 | 3,4-methylenedioxy-C₆H₃ | 2-(H₂N-CO)-C₆H₄- | Hydrochloride | $C_{20}H_{18}ClN_5O_5$ | 443.84 | 200 | 30 | Calc. % / Found % | 54.12 / 53.92 | 4.09 / 4.28 | 15.78 / 15.98 |
| 730192 | 3,4-methylenedioxy-C₆H₃ | 4-(morpholinyl-CO)-C₆H₄- | Hydrochloride | $C_{24}H_{24}ClN_5O_6$ | 513.93 | 260 | 22 | Calc. % / Found % | 56.09 / 56.28 | 4.51 / 4.69 | 13.62 / 13.69 |

The compounds of formula (I) have been tested on animals in the laboratory and have been shown to possess vasodilatatory, anti-ulcerous, respiratory analeptic, hypotensive, diuretic, antidepressive, analgesic, anti-inflammatory and neurotropic properties.

1. Vasodilatatory properties.

The compounds of formula I are capable of augmenting the flow of the coronary vessels of the isolated heart of a guinea-pig, when said compounds are added in the perfusion liquid of said organ.

By way of example, the following Table III lists the percentage augmentation of the flow of the isolated heart of a guinea-pig, obtained by the addition of certain compounds of formula I, in a concentration of 1 µg/ml, in the perfusion liquid.

TABLE III

| Code No. of Compound tested | Percentage augmentation of flow of isolated heart of guinea-pig (%) |
| --- | --- |
| 72 753 | 70 |
| 72 601 | 140 |
| 730056 | 50 |
| 730192 | 160 |
| 72 791 | 82 |

2. Anti-ulcerous properties.

The compounds of formula I, administered by intraduodenal means, reduce the extent of ulceration provoked by tying of the pylorus of a rat (Shay ulcers).

Thus, the compound of Code No. 72 722, administered by intraduodenal means, in a dose of 50 mg/Kg, provokes a reduction of Shay ulcers by 50%.

3. Respiratory analeptic properties.

The compounds of formula (I), administered by intraveinous or intraduodenal means to an anaesthetised guinea-pig, are capable of opposing the respiratory depression provoked by morphine.

By way of example, following the administration of 100 mg/Kg/i.d. of the compound of Code No. 72 262, there is observed in the anaesthetised guinea-pig a percentage augmentation of 140% in the amplitude of the respiratory movements.

As well, the administration of the compounds of Code No. 72 791 provokes, under the same conditions, an augmentation of 25% in the respiratory frequency and of 55% in the amplitude of the respiratory movements. Finally, following the administration of 100 mg/Kg/i.d. of the compound of Code No. 72 629, there is observed, in the anaesthetised guinea-pig, a percentage augmentation of 100% in the amplitude of the respiratory movements.

4. Hypotensive properties.

Administered by intraveinous means to the anaesthetised rat, the compounds of formula (I), provoke a lowering of the arterial pressure.

By way of example, the following Table (IV) lists the results obtained following the administration of 2mg/Kg/i.v. of different compounds of formula (I).

TABLE IV

| Code No. of compound tested | Percentage diminution of arterial pressure (%) | Duration of effect (mn) |
| --- | --- | --- |
| 72 262 | ≈35 | 30 |
| 730 192 | ≈60 | 50 |
| 72 629 | ≈70 | 45 |
| 72 795 | ≈35 | 20 |

5. Diuretic properties.

The compounds of formula (I), administered by oral means to the mouse, simultaneously with a volume of 1 ml of an isotonic solution of sodium chloride per 25 g. of the corporeal weight of the mouse, are capable of provoking an augmentation of the volume of urine emitted by reference to control animals, the volume being measured for 6 hours following administration.

Thus, the administration of 25 mg/Kg/p.o. of the compounds of Code Nos. 72 308 and 72 319, produced an augmentation of urinary elimination of 60 and 70%, respectively.

6. Anti-depressive properties.

The compounds of formula (I) preventatively administered by oral means to the mouse, are capable of opposing the ptosis provoked by the injection of reserpine.

Thus, following the administration of 100 mg/Kg/p.o. of the compound of Code No. 730 192, there is observed, in the mouse, a reduction of 55% in the ptosis provoked by the injection of reserpine.

7. Analgesic properties.

The compounds of formula (I) administered by oral means to the mouse, are capable of reducing the number of painful stretchings caused by the intraperitoneal injection of phenylbenzoquinone.

Thus, following the oral administration of 100 mg/Kg of the compounds of Code No. 72 635, there is observed a percentage diminution of 50% in the number of painful stretchings caused by the intraperitoneal injection of phenylbenzoquinone.

8. Anti-inflammatory properties.

These properties are shown by a diminution of the local oedema provoked in a rat by the sub-plantar injection of a phlogogenic agent, such as carraghenine, following the oral administration of the compounds of formula (I).

Thus, following the administration of the compound of Code No. 72 791, in a dose of 100 mg/Kg/p.o. there is observed a percentage diminution of the sub-plantar oedema of 65%.

9. Neurotropic properties.

a. Inhibitory action of monoamine oxidase:

The compounds of formula I, administered by oral means to the mouse pre-treated by an inhibitory substance of monoamine oxidase (I.M.A.O.), potentialising 5-hydroxytryptophane, tryptamine and DOPA ($\beta$-(3,4dihydroxyphenyl)-$\alpha$-alanine). -$\beta$- alanine).

Thus, the DE 50 of the compound of Code No. 72 553, in the potentialisation of 5-hydroxytryptophane, of tryptamine and that of DOPA, are respectively 24 mg/Kg/p.o., 35 mg/Kg/p.o. and 65 mg/Kg/p.o.

b. Antianoxic action.

This activity has been researched in the mouse in the oxyprive anoxia test and in the rat in the cortical electric silence (S.E.C.) test.

Oxyprive anoxia test on the mouse.

Injected by intraduodenal means, the compounds of formula I augment the survival time of mice placed in an enclosure short of oxygen.

By way of example, the administration of 100 mg/Kg/i.p. of the compound of Code No. 72 553 produced an augmentation of 54% of the survival time of mice placed in an enclosure short of oxygen.

Cortical electric silence test.

The compounds of formula I, injected by intraperitoneal means to an anaesthetised and curarised rat, placed under artificial respiration and subjected to anoxia with nitrogen, augmented the delay in appearance of the cortical electric silence.

Thus, there is observed a significant delay in the appearance of the S.E.C. following the administration of 100 mg/Kg/i.p. of the compound of Code No. 72 553 and a diminution in the recuperation time of cortical electrogenesis following the administration of a dose of 25 mg/Kg/i.p.

Amnesia tests provoked by oxyprive anoxia or by maximal electric shock.

Administered by intraperitoneal means, the compounds of formula I protect a rat subjected to a passive shunning test (box with two compartments of GIURGEA) from the amnesia effects of oxyprive anoxia or an electric shock.

By way of example, the administration of 100 mg/Kg/i.p. of the compound of Code No. 72 553 protected the rat against amnesia provoked by anoxia and by electric shock by 86 and 80% respectively.

This being, it may be remarked, that the compounds according to the invention possess original properties in relation to those of the compounds of formula (Io) described in the above-referenced application.

In effect, whilst the compounds of formula (Io) show essentially analgesic and anti-inflammatory properties and are deprived of cardiovascular and neurotropic activities, the compounds of the present invention possess vasodilatatory properties (augmentation of the flow of the coronary vessels of the isolated heart of a guinea-pig) and hypotensive properties (lowering of the arterial pressure of an anaesthetised rat) as well as interesting neurotropic properties since, as indicated above, they exercise a potentialisation action on 5-hydroxy-tryptophane, on tryptamine and on DOPA on the mouse pre-treated with I.M.A.O., manifest an antianoxic activity and are active in a memory test.

Furthermore the compounds of formula I have litle toxicity, in that there is not observed a single case of mortality following the administration of 2000 mg/Kg/p.o. of the above-described compounds.

It has resulted that, for the compounds of formula I, the difference between the pharmacologically active doses listed above and the lethal doses is sufficiently great to permit the application of these derivatives in therapeutics.

The compounds of formula I are useful in the treatment of circulatory insufficiencies, gastro-duodenal ulcers, respiratory insufficiencies, hypertensions, oedemas, depressions, diverse originating pains, painful inflammations and cerebral deficits.

They may be administered by oral means in the form of tablets, sugar-coated pills or gelules containing 50 to 400 mg. of active ingredient (1 to 6 a day), in the form of drops containing 0.5 to 5% of active ingredient (20 to 60 drops - 1 to 3 times a day), by parenteral means in the form of injectable ampoules containing 10 to 250 mg. of active ingredient (1 to 3 a day) or by rectal means in the form of suppositories containing 25 to 200 mg. of active ingredient (1 to 3 a day).

Accordingly, the present invention also comprises a therapeutic composition comprising a compound of the general formula I, together with a therapeutically acceptable carrier.

What we claim is:

1. A compound having the formula

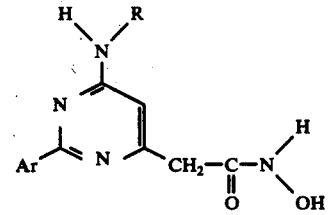

wherein R is 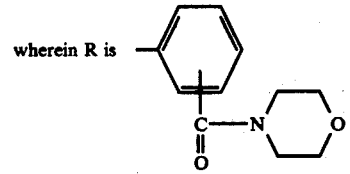

and Ar is phenyl substituted by one chloro, one fluoro, one trifluoromethyl, one methylenedioxy or one or more methoxy.

2. A compound as claimed in claim 1, in which Ar is p-chlorophenyl and R is 4-morpholinocarbonyl phenyl.

3. A compound as claimed in claim 1 in which Ar is m-trifluoromethyl phenyl and R is 4morpholinocarbonyl phenyl.

4. A compound as claimed in claim 1 in which Ar is 3,4-methylenedioxy phenyl and R is 4-morpholinocarbonyl phenyl.

5. A compound as claimed in claim 1 in which Ar is 3,4,5-trimethoxy phenyl and R is 4-morpholinocarbonyl phenyl.

6. A composition for treating a condition of circulatory insufficiency, gastro-duodenal ulcers, respiratory insufficiency, hypertension, edema, depression, pain, inflammation or cerebral deficit, comprising an effective amount of a compound as claimed in claim 1 for treating the condition, together with a therapeutically acceptable carrier.

* * * * *